United States Patent [19]

Asano et al.

[11] Patent Number: 5,250,420
[45] Date of Patent: Oct. 5, 1993

[54] METHOD AND REAGENT FOR DETERMINATION OF DEHYDROGENASE OR ITS SUBSTRATE

[75] Inventors: Shigeki Asano; Haruo Watanabe, both of Tsuruga; Yuzo Hayashi, Ashiya, all of Japan

[73] Assignee: Toyo Boseki Kabushiki Kaisha, Osaka, Japan

[21] Appl. No.: 746,202

[22] Filed: Aug. 15, 1991

Related U.S. Application Data

[63] Continuation of Ser. No. 177,354, Apr. 1, 1988, abandoned.

[30] Foreign Application Priority Data

Apr. 2, 1987 [JP] Japan .................................. 62-82277

[51] Int. Cl.⁵ ............................................. C12Q 1/32
[52] U.S. Cl. ........................................ 435/26; 435/14; 435/25; 435/28; 435/184; 435/810; 436/164; 436/904
[58] Field of Search ............... 435/4, 14, 25, 26, 28, 435/184, 810; 436/164, 904

[56] References Cited

U.S. PATENT DOCUMENTS 3,985,621 10/1976 Maruyama et al. ............. 435/26 X
4,394,444 7/1983 Cameron et al. ...................... 435/11
4,622,296 11/1986 Yamanishi et al. ................... 435/26
4,629,697 12/1986 Limbach et al. ..................... 435/26

FOREIGN PATENT DOCUMENTS 29104 5/1981 European Pat. Off. ............. 435/11
0124909 11/1984 European Pat. Off. ............. 435/26
0113181 7/1983 Japan .................................. 435/26

OTHER PUBLICATIONS

*Chemical Abstracts*, vol. 106, No. 13, p. 374 Abstract No. 99215r, Mar. 1987.

*Primary Examiner*—Mary E. Ceperley
*Assistant Examiner*—Carol A. Spiegel
*Attorney, Agent, or Firm*—Wegner, Cantor, Mueller & Player

[57] ABSTRACT

A method for determining dehydrogenase or its substrate in dehydrogenase reaction, which comprises subjecting a dehydrogenase and its substrate to dehydrogenase reaction in the presence of an electron carrier or a combination of a coenzyme and an electron carrier, allowing to form $H_2O_2$ through transfer of electrons derived from the substrate by the dehydrogenase reaction to $O_2$ via the electron carrier or via the coenzyme and electron carrier, stopping the dehydrogenase reaction, reacting said $H_2O_2$ with a peroxidase and a chromogen, and measuring a formed dye, and a reagent for determining dehydrogenase or its substrate. By the method and the reagent, dehydrogenase or its substrate can be accurately determined in a short time regardless of the concentration of the dehydrogenase and/or the substrate and without staining tubes or cells of a determination device with a dye.

19 Claims, 2 Drawing Sheets

METHOD AND REAGENT FOR DETERMINATION OF DEHYDROGENASE OR ITS SUBSTRATE

This application is a continuation of U.S. application Ser. No. 07/177,354, now abandoned, filed Apr. 1, 1988.

The present invention relates to a method for determining dehydrogenase or its substrate in the dehydrogenase reaction wherein the dehydrogenase or the substrate can be determined accurately and quickly regardless of its concentration without staining the determination device with dye or the like, and a reagent for use in the method for the determination of the dehydrogenase or its substrate.

PRIOR ART

There have been known various dehydrogenation reactions catalyzed by various dehydrogenases. For example, the reaction of converting glucose-6-phosphate into glucono-δ-lactone-6-phosphate and the reaction of converting lactic acid into pyruvic acid are catalyzed by glucose-6-phosphate dehydrogenase and lactate dehydrogenase, respectively. In these reactions, the determination of the enzyme or the substrate has been carried out by, for example, determining reduced coenzymes (e.g. NADH, NADPH and the like) which are generated by the reduction of coenzymes participating in these reactions (e.g. $NAD^+$, $NADP^+$ and the like). The determination of the enzyme or the substrate is carried out by measuring an absorbance of, for example, NADH. However, these methods have a disadvantage that the sensitivity is not sufficient. For this reason, there has been introduced a method where the enzyme or the substrate is determined in such a way that the above NADH is further converted into another compound to be measured. One of these methods is the following method utilizing formazan development:

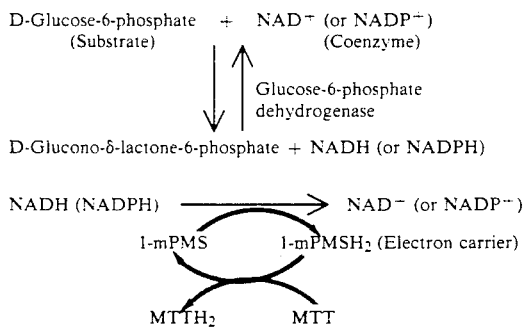

wherein 1-mPMS means 1-methoxy-5-methylphenazinium methylsulfate, 1-mPMSH₂ is a reduced type thereof, MTT means 3-(4,5-dimethylthiazol-2-yl)-2,5-diphenyltetrazolium bromide, and MTTH₂ is a reduced type thereof (formazan dye).

In the above reaction, NADH generated in the dehydrogenase reaction of D-glucose-6-phosphate to D-glucono-δ-lactone-6-phosphate is converted into $NAD^+$ by donating electrons to the electron carrier such as 1-mPMS (NADPH also reacts in the same manner). 1-mPMS is then reduced to 1-mPMSH₂. Subsequently, MTT present in the reaction system is reduced by the 1-mPMSH₂ to MTTH₂ or the formazan dye, purple coloring of which is measured with a spectrophotometer to determine the NADH, and thus the enzyme or the substrate is indirectly determined. In addition to the above 1-mPMS, the electron carrier also includes phenazine methosulfate (PMS), 9-dimethylaminobenzo-α-phenazoxonium (Meldola blue) and the like. The method by the measurement of formazan dye indeed has a higher sensitivity than that of the above method of the determination of NADH, but it also has a disadvantage that it is difficult to determine with an automatic analyzer since this dye strongly sticks to tubes or cells of the determination device In order to avoid the above stain with the dye, a method is disclosed in Japanese Patent First Publication (KOKAI) No. 83598/1985. According to the method, oxygen, peroxidase (POD) and chromogen [e.g. N-ethyl-N-(2-hydroxy-3-sulfopropyl)-m-toluidine (TOOS) and 4-aminoantipyrine (4-AA)] are present in the reaction system in place of MTT in the method by the measurement of formazan development. The former part of the reaction is the same as in the method by the determination of formazan development. The reaction after the formation of NADH is illustrated by the following reaction scheme wherein the electron carrier is 1-mPMS and the chromogen is a combination of TOOS and 4-AA.

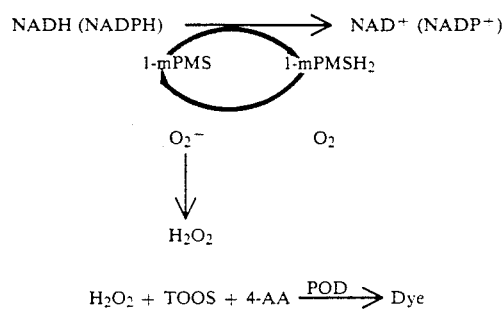

$$H_2O_2 + TOOS + 4\text{-}AA \xrightarrow{POD} Dye$$

Also in the above reaction system, the electrons are transferred from NADH to 1-mPMS to produce 1-mPMSH₂, which then transfers the electrons to O₂ present in the reaction system to form H₂O₂ via $O_2^-$. H₂O₂ acts on TOOS and 4-AA in the presence of peroxidase and thereby the chromogens are oxidized to produce a dye. Although this dye can be determined without stain of the determination device unlike the formazan dye, this method still has a disadvantage to be overcome. That is, the present inventors have tested the above method and have found that it has been difficult to obtain an accurate determination due to drastic color depression after the color development, especially in case of a high concentration of the substrate.

BRIEF SUMMARY OF THE INVENTION

An object of the present invention is to take away the above disadvantages and to provide a method by which the enzyme or its substrate in the dehydrogenase reaction can easily be determined in an accurate and simple manner without staining the determination device with the dye and the like. Another object of the present invention is to provide a method for the determination of the enzyme or its substrate in the dehydrogenase reaction regardless of their concentration in the test sample A further object of the present invention is to provide a reagent for use in the method for the determination of dehydrogenase or its substrate of the present invention. These and other objects and advantages of the present invention will be apparent to those skilled in the art from the following description.

DETAILED DESCRIPTION OF THE INVENTION

Figure 1:
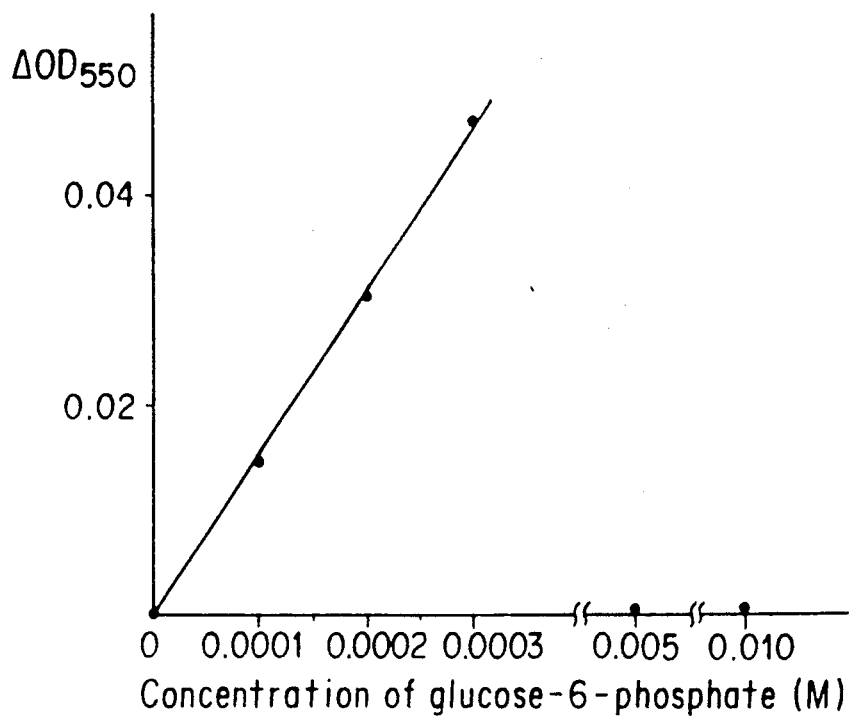
FIG. 1 shows a relationship between the absorbance ($\Delta OD_{550}$) and the concentration of the substrate glucose-6-phosphate (M) measured by the conventional method.

Before explaining the present invention, there are shown experimental results of the method described in the above Japanese Patent First Publication No. 83598/1985 which were carried out by the present inventors as follows:

[Experiment] Determination of glucose-6-phosphate

| Reaction components (1): | |
| --- | --- |
| Tris-hydrochloric acid buffer (pH 8.0) | 1.4 ml |
| Glucose-6-phosphate solution (0–0.01 M) | 0.1 ml |
| Glucose-6-phosphate dehydrogenase solution (0.5 U/ml) | 0.3 ml |
| NAD$^-$ solution (0.1 M) | 0.2 ml |
| 1-mPMS solution (0.5 mg/ml) | 0.1 ml |
| Reaction components (2): | |
| 4-Aminoantipyrine solution (10 mg/ml) | 0.3 ml |
| TOOS solution (10 mg/ml) | 0.3 ml |
| Peroxidase solution (100 U/ml) | 0.3 ml |

The above reaction components (1) were mixed and reacted at 37° C. for just 5 minutes and thereto the reaction components (2) were added and the mixture was reacted for further 4 minutes. The absorbance of this reaction mixture was measured at 550 nm. FIG. 1 shows a relationship between the substrate (glucose-6-phosphate) concentration and OD value (value obtained by deducting a value in blank from the found value; shown as $\Delta OD_{550}$).

As is clear from FIG. 1, a linear relationship between the substrate (glucose-6-phosphate) concentration and the OD value is observed at a relatively low concentration (below 0.0003 M) of the substrate, but in case of a high concentration (0.005 M and 0.010 M) of the substrate, an increase of the absorbance was not observed after 4 minutes as in the case of the concentration of 0 M due to drastic color depression after color development.

As a result of the present inventors' study, it is assumed that the drastic color depression of the developed dye in case of the high substrate concentration is due to the side reaction as shown in the following diagram 1, and further that in case of another type of reaction, i.e. a reaction of sarcosine dehydrogenase, where no coenzyme participates in the reaction, a reaction as shown in the following diagram 2 proceeds and hence the color depression occurs like that in the above glucose-6-phosphate dehydrogenase reaction.

Diagram 1

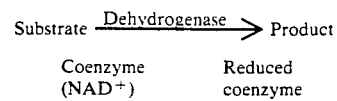

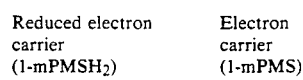

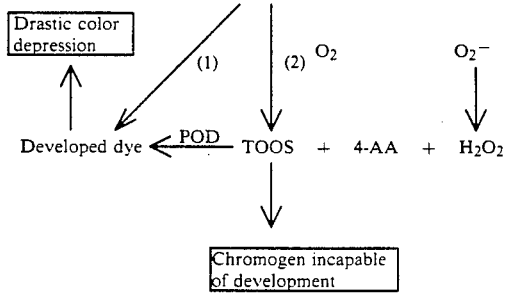

Diagram 2

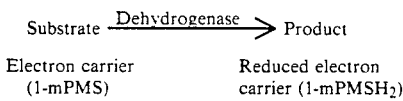

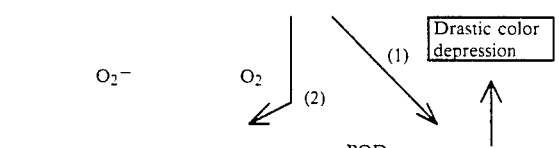

In the above diagram 1, electrons generated in the dehydrogenase reaction are transferred to the coenzyme and the electron transfer system, and then to $O_2$. However, when the substrate concentration is so high that the enzyme reaction is not stopped, (1) the electrons from the reduced electron carrier are transferred to the dye (formed by the reaction with peroxidase) not to $O_2$, which results in the drastic color depression, and (2) the electrons from the reduced electron carrier are not transferred to $O_2$ but to TOOS, and thereby TOOS is reduced and becomes incapable of color development, which results in poor color development. The above is the cause of the poor color development and the drastic color depression in the reaction system. The same principle as above will be applicable to the case of diagram 2. After taking these matters into consideration, the present inventors have found that the electrons from the electron transfer system could be transferred to $O_2$ completely (a) by setting the reaction system so that the dehydrogenase reaction and the formation of $H_2O_2$ are completed before the peroxidase reaction starts; and (b) by adding the chromogen after the dehydrogenase reaction is stopped.

Thus, the present invention relates to a method for determining a dehydrogenase or its substrate in a dehydrogenase reaction, which comprises subjecting a dehydrogenase and its substrate to dehydrogenase reaction in the presence of an electron carrier or a combination of a coenzyme and an electron carrier, allowing to form $H_2O_2$ through transfer of electrons derived from the substrate by the dehydrogenase reaction to $O_2$ via the electron carrier or via the coenzyme and electron carrier, stopping the dehydrogenase reaction, reacting said $H_2O_2$ with a peroxidase and a chromogen, and measuring a formed dye. The present invention relates further to a reagent for use in the determination of substrate of dehydrogenase, comprising (i) a dehydrogenase, (ii) an electron carrier or a combination of a coenzyme and an electron carrier, (iii) a stopping solution for the dehydrogenase reaction, (iv) a peroxidase and (v) a chromogen; and a reagent for use in the determination of dehydrogenase, comprising (i) a substrate of dehydrogenase, (ii) an electron carrier or a combination of a coenzyme and an electron carrier, (iii) a stopping solution for the hydrogenase reaction, (iv) a peroxidase and (v) a chromogen.

In accordance with the method of the present invention, dehydrogenase or its substrate in the dehydrogenase reaction can be determined in an accurate and simple manner by utilizing the oxidative development of the chromogen by peroxidase. Unlike the conventional method, which has difficulty in determining the substrate in a high concentration, the method of the present invention provides an accurate determination of the substrate regardless of its concentration. Since the dye formed in the reaction of the present invention does not stick to tubes or cells of the determination device, unlike formazan dye, it becomes possible to treat a large quantity of samples continuously with an automatic analyzer.

The terms "dehydrogenase" and "substrate" in the present invention mean such dehydrogenase and its substrate participating in the dehydrogenase reaction shown in the above diagrams 1 and 2, i.e. the reactions wherein the electrons from the substrate are transferred to $O_2$ via the electron carrier or via the coenzyme and the electron carrier to form $H_2O_2$. Typical examples of the dehydrogenase and its substrate are shown in Table 1. It is to be understood that the present invention is not limited to these combinations of the dehydrogenase and its substrate. Moreover, the substrate is not limited to those corresponding to each dehydrogenase but includes other substrates in so far as it can be specifically reacted with dehydrogenase.

TABLE 1

| Substrate | Dehydrogenase |
| --- | --- |
| Glucose | Glucose dehydrogenase (EC 1.1.1.47) |
| Glucose-6-phosphate | Glucose-6-phosphate dehydrogenase (EC 1.1.1.49) |
| Malate | Malate dehydrogenase (EC 1.1.1.37) |
| 3-α-Hydroxysteroid | 3-α-Hydroxysteroid dehydrogenase (EC 1.1.1.50) |
| Lactate | Lactate dehydrogenase (EC 1.1.1.27) |
| L-Glutamate | L-Glutamate dehydrogenase (EC 1.4.1.2) |
| Leucine | Leucine dehydrogenase (EC 1.4.1.9) |
| Sarcosine | Sarcosine dehydrogenase (EC 1.5.99.1) |
| Amine | Amine dehydrogenase (EC 1.4.99.3) |
| Succinic acid | Succinate dehydrogenase (EC 1.3.99.1) |
| Choline | Choline dehydrogenase (EC 1.1.99.1) |
| Fructose | Fructose dehydrogenase (EC 1.1.99.11) |
| Sorbitol | Sorbitol dehydrogenase (Japan. Pat. First Public. No. 2999/1981) |

The coenzyme employed in the method of the present invention includes $NAD^+$, $NADP^+$, flavins and the like. The flavins include flavin adenine dinucleotide (FAD), flavin mononucleotide (FMN) and the like. The dehydrogenation reaction involving the coenzyme includes those catalyzed by glucose dehydrogenase, glucose-6-phosphate dehydrogenase, malate dehydrogenase, 3-α-hydroxysteroid dehydrogenase, lactate dehydrogenase, L-glutamate dehydrogenase and leucine dehydrogenase among the dehydrogenases of the above Table 1. The concentration of the coenzyme is not particularly limited and is usually in the range of from 0.001 to 2000 mM.

Preferable electron carriers used in the method of the present invention include phenazine methosulfate (PMS), 1-methoxy-5-methylphenazium methylsulfate, 9-dimethylaminobenzo-α-phenazoxonium chloride and the like. These electron carriers may be used alone or in a mixture of more than one thereof. The concentration of the electron carrier in the reaction system is not specified but is usually in the range of from 0.0001 to 1.0 mg/ml.

The stopping solution for the hydrogenase reaction of the present invention includes an acid or an alkali, a buffer solution with different pH from that of the dehydrogenase reaction system, a dehydrogenase inhibitor, a surfactant, and the like. Suitable examples of the stopping solution are disclosed hereinafter.

The chromogen of the present invention may be any compound which is oxidized to develop color with $H_2O_2$ in the presence of peroxidase, including the following combinations:

(1) 4-Aminoantipyrine/aniline derivatives
(2) 4-Aminoantipyrine/phenol derivatives
(3) Benzothiazolinone hydrazone derivatives/aniline derivatives.

The aniline derivatives employed in the present invention include N-methyl-N-hydroxymethyl-3-methylaniline, N-ethyl-N-hydroxyethyl-3-methylaniline, N-ethyl-N-hydroxyethyl-3-ethylaniline, N-methyl-N-hydroxyethyl-3-methylaniline, N-methyl-N-hydroxypropyl-3-methylaniline, N-ethylN-hydroxypropyl-3-methylaniline, N-methyl-N-hydroxyethyl-3-ethylaniline, N-propyl-N-hydroxyethyl-3-methylaniline, N-methyl-N-hydroxyethyl-3-propylaniline, N,N-bis(β-hydroxyethyl)-3-methylaniline, N,N-bis(β-hydroxypropyl)-3-methylaniline, N,N-dimethyl-3-methylaniline, N,N-dimethyl-3-ethylaniline, N,N-dimethyl-3-propylaniline, N,N-diethyl-3-methylaniline, N,N-diethyl-3-ethylaniline, N,N-dipropyl-3-methylaniline, N-ethyl-N-(β-methanesulfonamidethyl)-m-toluidine, N-ethyl-N-(β-acetamidethyl)-3-methylaniline, N,N-dimethylaniline, N,N-diethylaniline, N,N-diisopropylaniline, N-methyl-N-hydroxyethylaniline, N-ethyl-N-hydroxyethylaniline, N-ethyl-N-sulfopropyl-m-toluidine, N- ethyl-N-(2-hydroxy-3-sulfopropyl)-m-toluidine, N-ethyl-N-(2-hydroxy-3-sulfopropyl)-m-anisidine, N-ethyl-N-(2-hydroxy-3-sulfopropyl)aniline, 3,5-dimethoxy-N-ethyl-N-(2-hydroxy-3-sulfopropyl)aniline, 3,5-dimethyl-N-ethyl-N-(2-hydroxy-3-sulfopropyl)aniline, N-ethyl-N-sulfopropyl-m-anisidine, N-ethyl-N-sulfopropyl-3,5-diemthylaniline, N-ethyl-N-sulfopropyl-3,5-dimethoxyanile, and the like.

The phenol derivatives include p-chlorophenol, p-bromophenol, 3,5-dichlorophenolsulfonic acid, 3-hydroxy-2,4,6-triiodobenzoic acid, and the like.

The benzothiazolinone hydrazone derivatives include 3-methyl-2-benzothiazolinone hydrazone and the like.

The concentration of the aniline derivatives and the phenol derivatives is not specified but is most preferably in the range of from 0.1 to 20 mM. 4-Aminoantipyrine is preferably used in a concentration of from about 1 to about 20 mM. The benzothiazolinone hydrazone derivatives are preferably used in a concentration of from about 0.1 to about 2 mM.

As already mentioned hereinabove, the agent for determining substrate of dehydrogenase of the present invention comprises the first reagent containing (i) a dehydrogenase and (ii) an electron carrier or a combination of a coenzyme and an electron carrier, the second reagent containing (iii) a stopping solution for the dehydrogenase reaction, and the third reagent containing (iv) a peroxidase and (v) a chromogen. The second reagent and the third reagent may be mixed together before using. The agent for determining dehydrogenase of the present invention comprises the first reagent containing (i) a substrate of dehydrogenase and (ii) an electron carrier or a combination of a coenzyme and an electron carrier, the second reagent containing (iii) a stopping solution for the dehydrogenase reaction, and the third reagent containing (iv) a peroxidase and (v) a chromogen. The second reagent and the third reagent may be mixed together before using.

For measuring the dehydrogenase or the substrate by the method of the present invention, the substrate, the dehydrogenase, the electron carrier and, if necessary, the coenzyme are mixed in the reaction mixture to carry out the dehydrogenase reaction. The electrons generated from the substrate are transferred to the coenzyme and the electron carrier (diagram 1) or to the electron carrier (diagram 2). The electrons are then transferred from the electron carrier to $O_2$, which is converted into $H_2O_2$ via $O_2^-$. Then the reaction system is kept under fixed conditions and the dehydrogenase reaction is stopped.

For stopping the hydrogenase reaction, the following methods may be employed but the present invention is not limited to these methods.

1) METHOD BY ADDING AN ACID OR AN ALKALI

Generally enzymes show a different stability depending on a pH value. That is, enzymes cannot exhibit their activities at a pH range higher or lower than a certain pH value. This property of enzymes suggests that the dehydrogenase reaction can be stopped by adding an acid or an alkali to the reaction system to alter the pH value of the reaction system so that the pH value falls into the pH range in which the enzymes cannot exhibit their activities. The acid or the alkali mentioned herein includes, for example, hydrochloric acid, sulfuric acid, phosphoric acid, acetic acid, nitric acid, sodium hydroxide, potassium hydroxide, aqueous ammonium, and the like, but the present invention is not limited to these acids and alkalis.

2) METHOD BY ADDING A BUFFER SOLUTION WITH A DIFFERENT PH VALUE FROM THAT OF THE DEHYDROGENASE REACTION SYSTEM

Alternatively, the pH value of the dehydrogenase reaction system may be altered in which the enzymes cannot exhibit their activities by mixing a buffer solution having a different pH value from that of the reaction system, instead of adding an acid or an alkali as above (1), and thereby the dehydrogenase reaction can be stopped. For example, when a dehydrogenase reaction is conducted in an acetate buffer solution (pH 4), a borate buffer (pH 10) is added to alter the pH value of the reaction system to pH 8, by which the dehydrogenase reaction is stopped. The buffer includes any conventional buffers so far as they can be employed in usual enzyme reactions.

3) METHOD BY ADDING A DEHYDROGENASE INHIBITOR TO THE REACTION SYSTEM

As is well known, activities of enzymes are inhibited by various compounds, some of which can completely deactivate activate enzymes. By adding such inhibitors, the dehydrogenase reaction may also be ceased. For example, in case of sarcosine dehydrogenase, an addition of an aqueous p-chloromercurybenzoate leads to a complete deactivation of the dehydrogenase. Also in case of fructose dehydrogenase, activities of the enzyme can be competely inhibited by adding mercury chloride. The inhibitor is not limited to p-chloromercurybenzoate or mercury chloride but may be any conventional compounds so far as they can inhibit the dehydrogenase reaction and deactivate enzymes.

4) METHOD BY ADDING A SURFACTANT

Enzymes are proteins having a three dimensional steric structure, and when the enzymes lose this steric structure, they cannot show their activities. Therefore, by adding a substance which can destroy the steric structure of enzymes (i.e. dehydrogenase), it is possible to deactivate the dehydrogenase and to inhibit the dehydrogenase reaction so that the dehydrogenase reaction ceases. Such a substance capable of destroying the steric structure of dehydrogenase includes a surfactant such as sodium dodecyl sulfate (SDS), sodium dodecylbenzene sulfonate and lithium dodecyl sulfate. The surfactant is not limited to the above exemplified surfactants, but includes any conventional surfactants which can deactivate the enzymes.

After the reaction is stopped, the chromogen and peroxidase are added to the reaction system. The dye formed by the reaction with peroxidase is usually measured by an optical means employing a spectrophotometer.

Since the dehydrogenation reaction is stopped in the method of the present invention, the reduced electron carrier (e.g. 1-mPMSH$_2$) does not remained in the reaction system regardless of the substrate concentration. Therefore, in the method of the present invention, there are not such disadvantages that the electrons from the reduced electron carrier are transferred to the chromogen and thereby the chromogen is reduced and becomes incapable of color development, and that said electrons act on the dye formed from the chromogen and thereby decolorize the dye. This means that the method of the present invention can provide an accurate determination at any concentration of the substrate without inducing depression of the dye. Further, the dye formed by the method of the present invention, unlike the formazan dye, does not stick to tubes or cells of the determination device and thus enables a mass-treatment of test samples in a short time by employing an automatic analyzer. Furthermore, it is a great advantage that dehydrogenase or its substrate can be determined by the method of the present invention at a concentration of more than 0.005 M, which concentration could never be determined by the conventional method.

The present invention is more specifically illustrated by the following Examples. However, it should be understood that the present invention is not limited to such Examples, but various changes and modifications can be made without departing from the scope and spirit of the invention.

| Example 1 (Determination of glucose-6-phosphate) | |
|---|---|
| Reaction components (1): | |
| Tris-hydrochloric acid buffer (pH 8.0) | 1.3 ml |
| Glucose-6-phosphate dehydrogenase (EC 1.1.1.49) solution (0.5 U/ml) | 0.1 ml |
| Glucose-6-phosphate solution (0–0.01 M) | 0.3 ml |
| NAD$^+$ solution | 0.2 ml |
| 1-mPMS solution (0.5 mg/ml) | 0.1 ml |
| Reaction components (2): | |
| 4-Aminoantipyridine solution (10 mg/ml) | 0.3 ml |
| TOOS solution (10 mg/ml) | 0.3 ml |
| Peroxidase solution (100 U/ml) | 0.3 ml |

Figure 2:
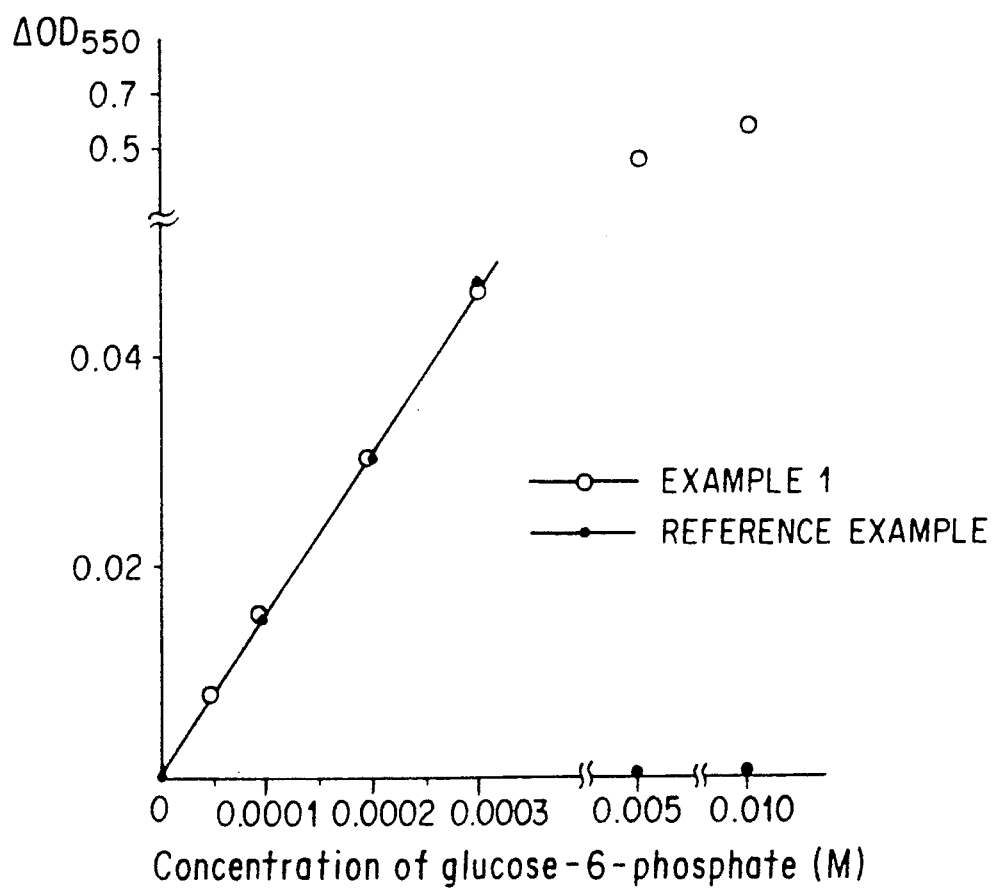
FIG. 2 shows a relationship between the absorbance ($\Delta OD_{550}$) and the concentration of the substrate glucose-6-phosphate (M) measured by the method of the present invention as compared with the conventional method.

The above reaction components (1) (pH 8.0) were mixed and reacted at 37° C. for just 5 minutes. Thereto an aqueous SDS solution (300 mg/ml) was added to stop the dehydrogenase reaction. Then the above reaction components (2) were added and the mixture was reacted for further 4 minutes, and then the absorbance of the reaction mixture was measured at 550 nm. FIG. 2 shows a relationship between the concentrations of the substrate glucose-6-phosphate and the OD values after the reaction (obtained by deduction of blank value from the found value; designated as $\Delta OD_{550}$).

REFERENCE EXAMPLE

The dehydrogenation reaction of Example 1 was repeated in the same reaction system as the reaction components (1) except that 1.4 ml of Tris-hydrochloric acid buffer was employed. After the reaction for just 5 minutes, the reaction components (2) (the same as in Example 1) were immediately added to the mixture, and the mixture was reacted for 4 minutes. The absorbance of the reaction mixture was measured at 550 nm, results of which are shown in FIG. 2.

As shown in FIG. 2, it is clear that the accurate determination is possible by the method of the present invention even if the substrate concentration is at a high level. On the contrary, the conventional method can determine the substrate only at a low level of the substrate but cannot determine the substrate at a high level (more than about 0.005 M) due to color depression leading to the absorbance with no significant difference from that at the substrate concentration of 0 M.

| Example 2 (Determination of activity of sarcosine dehydrogenase) | |
|---|---|
| Reaction components (1): | |
| Tris-hydrochloric acid buffer (pH 8.0) | 1.4 ml |
| Sarcosine dehydrogenase (EC 1.5.99.1) solution | 0.1 ml |
| Sarcosine solution (1 M) | 0.1 ml |
| 1-mPMS solution (0.5 mg/ml) | 0.1 ml |

Figure 3:
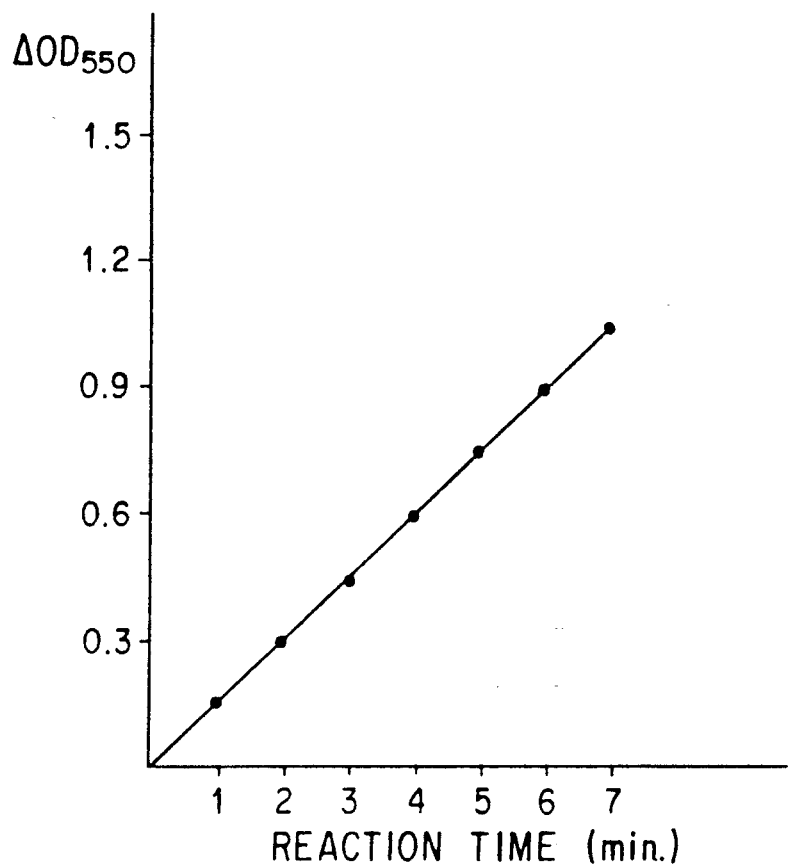
FIG. 3 shows the absorbance ($\Delta OD_{550}$) measured at various reaction times in the method of the present invention.

The above reaction components (1) (pH 8.0) were mixed and reacted at 37° C. for 1 minutes. Thereto an aqueous p-chloromercurybenzoate (0.1 M, 0.1 ml) was added to stop the dehydrogenase reaction. Then the reaction components (2) (the same as in Example 1) were added to the mixture. The reaction was conducted for 4 minutes and then the absorbance of the reaction mixture was measured at 550 nm. The above procedures were repeated except that the reaction was conducted for 2, 3, 4, 5, 6 and 7 minutes. FIG. 3 shows a relationship between the reaction time and the OD values (obtained by deduction of blank value from the found value; designated as $\Delta OD_{550}$). As is clear from FIG. 3, the enzyme activity of sarcosine dehydrogenase is accurately determined by the method of the present invention.

| Example 3 (Determination of activity of fructose dehydrogenase) | |
|---|---|
| Reagent 1: | |
| Fructose | 1 M |
| m-PMS | 10 mM |
| 4-AA | 1 mg/ml |
| McIlvaine's buffer solution (pH 4.5) | |
| Reagent 2 | |
| TOOS | 1 mg/ml |
| TES (N-tris(hydroxymethyl)methyl-2-aminoethanesulfonic acid) buffer solution (pH 7.5) | |
| Reagent 3 | |
| Sodium dodecyl sulfate (SDS) | 10% |

Fructose dehydrogenase solutions (0–20 ml) were subjected to fructose dehydrogenase measurement employing the above reagents 1 to 3.

Figure 4:
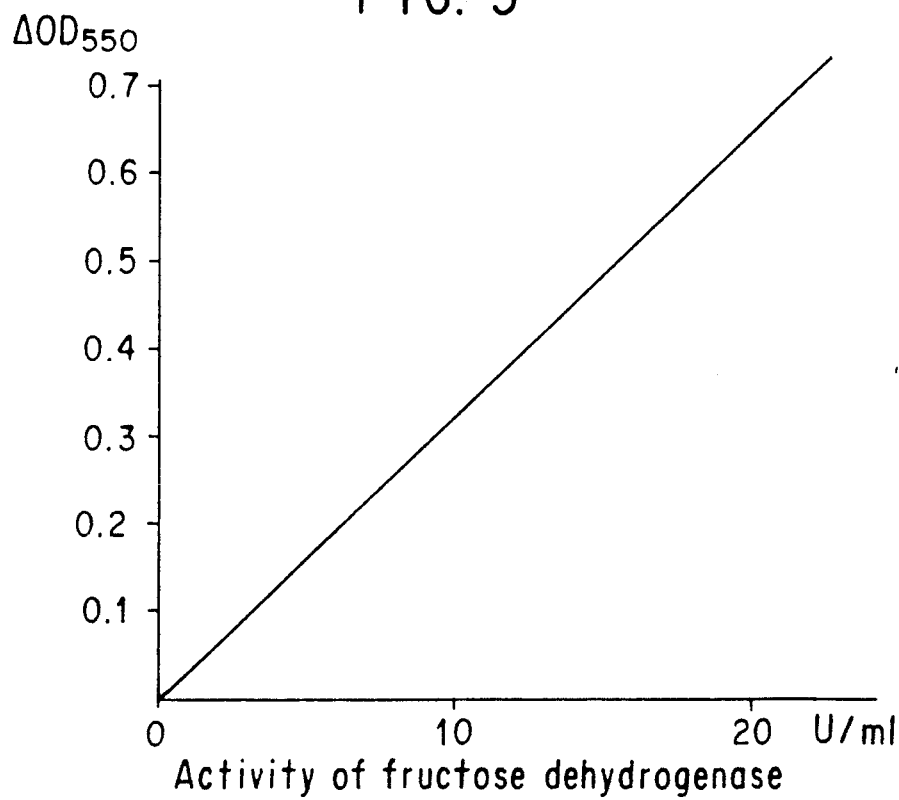
FIG. 4 shows a relationship between the fructose dehydrogenase activity and the absorbance ($\Delta OD_{550}$) of the reaction solution when measuring the fructose dehydrogenase activity by the method of the present invention.

First, the reagent 1 was taken into a test tube and pre-incubated at 37° C. Thereto a fructose dehydrogenase solution was added and reacted at 37° C. for 5 minutes. After the reaction, the reagent 3 was added to the reaction mixture to stop the reaction and then the reagent 2 (1 ml) was added. Five minutes after the addition of the reagent 2, the absorbance of the reaction mixture was measured at 550 nm with control of blank. As a result, as shown in FIG. 4, the graph was a straight line. Thus, it was proved that the fructose dehydrogenase activity was correctly measured.

What is claimed is:

1. A method for determining a dehydrogenase or its substrate in a dehydrogenase reaction, comprising the steps of:

(a) mixing of dehydrogenase and its substrate in the presence of an electron carrier or a combination of a coenzyme and an electron carrier, such that $H_2O_2$ is formed through transfer of electrons derived from the substrate by the dehydrogenase reaction to $O_2$ via the electron carrier or via the coenzyme and electron carrier;

(b) adding a stopping reagent to the mixture of step (a) such that the dehydrogenase reaction is terminated by the addition of said reagent;

(c) adding a peroxidase and a chromogen which is oxidized to develop color with $H_2O_2$ in the presence of peroxidase to the mixture of step (b) such that the $H_2O_2$ oxidizes the chormogen to be oxidized with $H_2O_2$ to produce a dye and wherein step (c) is performed simultaneously or subsequently to step (b); and (d) measuring said dye and correlating said dye measurement to the present of said dehydrogenase or its substrate.

2. The method according to claim 1, wherein the dehydrogenase reaction is stopped by deactivating the dehydrogenase.

3. The method according to claim 2, wherein the dehydrogenase is deactivated by adding an acid or an alkali according to step (b).

4. The method according to claim,2, wherein the dehydrogenase is deactivated by changing the pH value of the reaction according to step (b) with a buffer solution having a different pH value.

5. The method according to claim 2, wherein the dehydrogenase is deactivated by adding a surfactant to the reaction according to step (b).

6. The method according to claim 2, wherein the dehydrogenase is deactivated by adding a dehydrogenase inhibitor to the reaction according to step (b).

7. The method according to claim 5, wherein the surfactant is sodium dodecyl sulfate.

8. The method according to claim 5, wherein the surfactant is sodium dodecylbenzene sulfonate.

9. The method according to claim 1, wherein the coenzyme is a member selected from the group consisting of $NAD^+$, $NADP^+$ and flavins.

10. The method according to claim 1, wherein the dehydrogenase is a member selected from the group consisting of glucose $\alpha$-dehydrogenase, glucose-6-phosphate dehydrogenase, malate dehydrogenase, 3-$\alpha$-hydroxysteroid dehydrogenase, lactate dehydrogenase, L-glutamate dehydrogenase, leucine dehydrogenase, sarcosine dehydrogenase, amine dehydrogenase, succinate dehydrogenase, choline dehydrogenase, fructose dehydrogenase and sorbitol dehydrogenase.

11. The method according to claim 1, wherein the electron carrier is a member selected from the group consisting of phenazine methosulfate, 1-methoxy-5-methylphenazium methylsulfate and dimethylaminobenzo-$\alpha$-phenazoxonium chloride.

12. The method according to claim 1, wherein the chromogen which is oxidized to develop color with $H_2O_2$ in the presence of peroxidase is a color-forming pair combination selected from the group consisting of 4-aminoantipyrine/aniline derivatives, 4-aminoantipyrine/phenol derivatives and benzothiazolinone hydrazone derivative/aniline derivatives.

13. The method of claim 1, further comprising using a reagent system consisting essentially of (i) the dehydrogenase or the substrate for the dehydrogenase, (ii) the electron carrier or the coenzyme and the electron carrier, (iii) the stopping reagent for the dehydrogenase reaction, (iv) the peroxidase and (v) the chromogen which is oxidized to develop color with $H_2O_2$ in the presence of the peroxidase.

14. A reagent system for determining a substrate of a dehydrogenase, comprising a first reagent containing a combination of (i) the dehydrogenase and (ii) an electron carrier or a combination of a coenzyme and an electron carrier; and a second reagent containing (iii) a stopping reagent for the dehydrogenase reaction; and a third reagent containing a combination of (iv) a peroxidase and (v) a chromogen which is oxidized to develop color with $H_2O_2$ in the presence of peroxidase.

15. A reagent system for determining a dehydrogenase, comprising a first reagent containing a combination of (i) a substrate of the dehydrogenase and (ii) and electron carrier or a combination of a coenzyme and an electron carrier; and a second reagent containing (iii) a stopping reagent for the dehydrogenase reaction; and a third reagent containing a combination of (iv) a peroxidase and (v) a chromogen which is oxidized to develop color with $H_2O_2$ in the presence of peroxidase.

16. The reagent system for determining the dehydrogenase according to claim 15, which comprises (i) the substrate of the dehydrogenase, (ii) the electron carrier, (iii) the stopping reagent for the dehydrogenase reaction, (iv) the peroxidase and (v) the chromogen which is oxidized to develop color with $H_2O_2$ in the presence of peroxidase.

17. The reagent system for determining the dehydrogenase according to claim 15, which comprises (i) the substrate of the dehydrogenase, (ii) the coenzyme and the electron carrier, (iii) the stopping reagent for the dehydrogenase reaction, (iv) the peroxidase and (v) the chromogen which is oxidized to develop color with $H_2O_2$ in the presence of peroxidase.

18. A reagent system for determining a substrate of a dehydrogenase, comprising a first reagent containing a combination of (i) the dehydrogenase and (ii) and electron carrier or a combination of a coenzyme and an electron carrier; and a second reagent containing a combination of (iii) a stopping reagent for the dehydrogenase reaction, (iv) a peroxidase and (v) a chromogen which is oxidized to develop color with $H_2O_2$ in the presence of peroxidase.

19. A reagent system for determining a dehydrogenase, comprising a first reagent containing a combination of (i) a substrate of the dehydrogenase and (ii) an electron carrier or a combination of a coenzyme and an electron carrier; and a second reagent containing a combination of (iii) a stopping solution for the dehydrogenase reaction, (iv) a peroxidase and (v) a chromogen which is oxidized to develop color with $H_2O_2$ in the presence of peroxidase.

* * * * *